United States Patent [19]

Julius et al.

[11] Patent Number: 5,856,494
[45] Date of Patent: Jan. 5, 1999

[54] PREPARATION OF 2, 2, 6, 6-TETRAMETHYLPIPERIDIN-4-ONE (TAA)

[75] Inventors: Manfred Julius, Limburgerhof; Dieter Hermeling, Böhl-Iggelheim; Hardo Siegel, Speyer; Wolfgang Harder, Weinheim, all of Germany

[73] Assignee: BASF Aktiengesellschaft, Ludwigshafen, Germany

[21] Appl. No.: 911,456

[22] Filed: Aug. 14, 1997

[30] Foreign Application Priority Data

Aug. 23, 1996 [DE] Germany ............... 196 34 157.4

[51] Int. Cl.⁶ .................................................. C07D 211/74
[52] U.S. Cl. ................................................................ 546/242
[58] Field of Search ............................................. 546/242

[56] References Cited

U.S. PATENT DOCUMENTS

| | | | |
|---|---|---|---|
| 3,959,295 | 5/1976 | Orban et al. | 260/293 |
| 4,356,308 | 10/1982 | Wiezer et al. | 546/242 |
| 4,536,581 | 8/1985 | Cantatore et al. | 546/242 |
| 4,734,502 | 3/1988 | Kruse | 546/242 |

FOREIGN PATENT DOCUMENTS

| | | |
|---|---|---|
| 004104 | 9/1979 | European Pat. Off. . |
| 074 607 | 3/1983 | European Pat. Off. . |
| 2916471 | 4/1979 | Germany . |
| 479 049 | 3/1978 | Italy . |
| 2047681 | 12/1980 | United Kingdom . |
| 2176777 | 1/1987 | United Kingdom . |

OTHER PUBLICATIONS

Kinishi et al. "2,2,6,6–tetramethyl–4–oxopiperidine" CA 107:58879, 1987.

Balogh et al. "2,2,6,6–tetramethyl–4–piperidinone" CA 107:178627, 1987.

*Primary Examiner*—Ceila Chang
*Attorney, Agent, or Firm*—Keil & Weinkauf

[57] ABSTRACT

A process for preparing 2,2,6,6-tetramethylpiperidin-4-one (TAA) is described, wherein a mixture comprising acetone and/or acetone condensates and ammonia in a molar ratio of from 20:1 to 3:1 at from 50° to 130° C.

is reacted in the presence of dimethyl sulfate, the amount of dimethyl sulfate being from 0.5 to 5 mol-%, based on acetone.

5 Claims, No Drawings

PREPARATION OF 2, 2, 6, 6-TETRAMETHYLPIPERIDIN-4-ONE (TAA)

Preparation of 2,2,6,6-tetramethylpiperidin-4-one (TAA)

The invention relates to a process for preparing 2,2,6,6-tetramethylpiperidin-4-one (TAA).

Triacetoneamine (2,2,6,6-tetramethylpiperidin-4-one; TAA) can be prepared is by reacting acetone or acetone-containing solutions of acetone follow-on products or condensation products, such as mesityl oxide, diacetone alcohol, diacetoneamine, acetonin or phorone, with ammonia in a cyclocondensation reaction.

The synthesis can be carried out in one or two stages. The two-stage process is less cost-effective. In that process, the synthesis of the TAA proceeds via acetonin as an intermediate.

The more cost-effective one-stage synthesis can be carried out under both homogeneous and heterogeneous catalysis. The reaction temperatures employed in this synthesis are usually within the range from 50° to 100° C.

EP-B 0 004 104 discloses a process for preparing TAA which involves reacting acetone and ammonia in a molar ratio of from 2:1 to 25:1 in the presence of a solid acidic catalyst at from 80° C. to 130° C. under the autogenous pressure of the system, which may also be increased by adding inert gas. The solid acidic catalysts employed in this known process are virtually insoluble in both the starting materials and the reaction mixture. Catalysts which are so solid offer the advantage that their chemical stability is very high. Moreover, this known process can be carried out continuously. Nevertheless, the process is disadvantageous insofar as the yields obtained are low, being situated at about 19% based on the acetone employed.

Other known TAA syntheses are conducted under batchwise conditions, resulting in increased effort and time (cf. eg. DE-C 29 10 761).

In the batchwise processes, various catalysts have been employed, examples being Lewis acids, Brönstedt acids, halogen compounds, etc. A common feature of all these processes is that the catalyst has, with great effort, to be separated off and removed after the reaction has been carried out. Using, for example, calcium chloride (cf. ES-A 479 049), relatively large amounts of aqueous calcium chloride solution are obtained in the reaction, and this solution, owing to its contamination with organic substances, is difficult to eliminate.

Similar difficulties result when TAA is synthesized using catalysts from the class of the halogen compounds. The resulting waste materials are particularly problematic from an environmental standpoint.

It is an object of the present invention to provide a process, especially a continuous process, in which the synthesis product TAA is obtained in high yield but with a reduction in time and effort. Furthermore, in view of the problems set out above, the process should be less problematic from the environmental standpoint.

We have found that this object is achieved by a process for preparing TAA that comprises reacting a mixture containing acetone and/or acetone condensates and ammonia in a molar ratio of from 20:1 to 3:1 in the presence of dimethyl sulfate at from 50° to 130° C., the amount of dimethyl sulfate being from 0.5 to 5 mol-% based on acetone.

The subclaims relate to preferred embodiments.

The focus of the invention is that dimethyl sulfate ($H_3C$—$OSO_3$—$CH_3$; DMS) is an excellent catalyst for the synthesis of TAA from acetone and ammonia. This catalyst simultaneously meets all of the above-mentioned requirements. It is readily soluble in acetone and ammonia, and thus also has good metering qualities. In addition, the catalyst is inexpensive. Further, when the synthesis is carried out using this catalyst the discharges from the reaction are homogeneous and free from halogen, which is a distinct advantage from the environmental standpoint in particular.

In the novel process the dimethyl sulfate is employed in an amount of from 0.5 to 5 mol-% based on acetone. The molar ratio of acetone to ammonia in the reaction mixture is from 20:1 to 3:1, but preferably from 10:1 to 3:1. Particularly good selectivities of the reaction are obtained at a molar ratio of acetone to ammonia in the range from 10:1 to 6:1. If the reaction mixture contains acetone condensates, then these are converted to acetone; for example, 1 mol of mesityl oxide corresponds to 2 mol of acetone.

In addition, the novel process is also outstandingly suited to continuous synthesis. In this case the pressure is set such that all of the components are in liquid form under the reaction conditions; with continuous operation at from 50° C. to 100° C., then, the pressure is in a range of 10–100 bar [$1\times10^6$–$1\times10^7$ Pa]. Moreover, acetone is not the only starting material which can be employed in the novel process. Rather, acetone follow-on products, especially follow-on products obtained by condensation, such as mesityl oxide, diacetone alcohol, diacetoneamine, acetonin or phorone, can also be employed, alone or as a mixture in combination with acetone.

The invention is illustrated in more detail below by means of examples:

I. Noncontinuous synthesis of TAA

EXAMPLE 1

30.2 mol of acetone and 0.60 mol of dimethyl sulfate were charged to a 3.5 l stainless-steel autoclave. The autoclave was rendered inert with nitrogen, 4.5 mol of ammonia were injected, and the reaction mixture was heated at 60° C. with intense stirring. A pressure of about 5 bar was established.

After a reaction time of 4 h, the autoclave was cooled to room temperature and let down, and the reaction discharge was analyzed by gas chromatography.

| Reaction | Experiment A | | Experiment B | |
|---|---|---|---|---|
| discharge: | 1861.8 g | | 1870.9 g | |
| composition: | GC area % | % by weight | GC area % | % by weight |
| Acetone | 47.5 | 45.1 | 50.0 | 47.0 |
| TAA | 32.8 | 23.5 | 31.0 | 20.1 |
| Acetonin | 0.0 | 0.0 | 0.1 | <0.1 |
| Mesityl oxide | 8.8 | 5.2 | 8.2 | 5.1 |
| Water | | 9.9 | | 9.6 |
| N-containing by-product | 4.5 | | 4.9 | |
| Further by-products | 6.4 | | 5.8 | |

This gives a mean TAA yield of 26.0%, based on acetone employed, for an acetone conversion of 51.0%.

EXAMPLE 2

The analogous reaction of 30.2 mol of acetone in accordance with Example 1 but with a different amount of ammonia, now 3.0 mol, gave the following results after analysis of the reaction mixture by gas chromatography:

| Reaction | Experiment A | | Experiment B | |
|---|---|---|---|---|
| discharge: composition: | 1850.6 g GC area % | % by weight | 1852.7 g GC area % | % by weight |
| Acetone | 57.4 | 55.2 | 60.7 | 57.4 |
| TAA | 27.4 | 18.5 | 23.2 | 14.5 |
| Acetonin | 0.0 | 0.0 | 0.0 | 0.0 |
| Mesityl oxide | 7.9 | 4.9 | 8.8 | 5.4 |
| Water | | 7.9 | | 7.3 |
| N-containing by-product | 2.8 | | 3.1 | |
| Further by-products | 4.5 | | 4.2 | |

This gives a mean TAA yield of 19.6%, based on acetone employed, for an acetone conversion of 40.6%.

II. Continuous synthesis of TAA

EXAMPLE 3

A feed stream mixed beforehand from two part-streams comprising 19.8 g/h of a solution containing 2.0 mol-% of dimethyl sulfate in acetone and 1.25 g/h of ammonia was introduced at the base of a pressure-resistant stirred-kettle reactor with a volume of 184 cm$^3$, while the reaction discharge was taken off continuously from the top of the reactor. The reactor was operated in flooded manner; the pressure was 14 bar. The contents of the reactor were mixed intensively by means of a disk stirrer, and the reactor was heated in an oil bath such that the reaction mixture was at 60° C. The material flowing off the reactor was checked in a downstream viewing cell (volume 5 ml) under reaction conditions in terms of pressure and temperature for its single-phase nature. The homogeneous reaction discharge was let down under pressure regulation in a phase separator, and was collected and subjected to analysis by gas chromatography.

| Reaction discharge: composition: | 21.5 g/h GC area % | % by weight |
|---|---|---|
| Acetone | 48.2 | 45.5 |
| Ammonia | | 0.05 |
| TAA | 34.2 | 22.3 |
| Acetonin | 0.3 | 0.2 |
| Mesityl oxide | 6.8 | 4.2 |
| Water | | 10.3 |
| N-containing by-product | 3.5 | |
| Further by-products | 7.0 | |

This gives a TAA yield of 27.9%, based on acetone employed, for an acetone conversion of 49.5%.

We claim:

1. A process for preparing 2,2,6,6-tetramethylpiperidin-4-one (TAA) which comprises subjecting a mixture comprising acetone and/or acetone condensates and ammonia in a molar ratio of from 20:1 to 3:1 at from 50° to 130° C.

to reaction in the presence of dimethyl sulfate, the amount of dimethyl sulfate being from 0.5 to 5 mol-%, based on acetone.

2. A process as claimed in claim 1, wherein the molar ratio of acetone and/or acetone condensates to ammonia is from 10:1 to 3:1.

3. A process as claimed in claim 1, wherein the reaction is carried out continuously.

4. A process as claimed in claim 1, wherein the reaction mixture is in liquid form.

5. A process as claimed in claim 1, wherein the acetone condensates comprise mesityl oxide, diacetone alcohol, diacetoneamine, acetonin or phorone.

* * * * *